(12) United States Patent
Singer

(10) Patent No.: US 8,704,510 B2
(45) Date of Patent: *Apr. 22, 2014

(54) METHOD AND APPARATUS FOR MAGNETIC RESPONSE IMAGING

(71) Applicant: Jerome R. Singer, Berkeley, CA (US)

(72) Inventor: Jerome R. Singer, Berkeley, CA (US)

(*) Notice: Subject to any disclaimer, the term of this patent is extended or adjusted under 35 U.S.C. 154(b) by 4 days.

This patent is subject to a terminal disclaimer.

(21) Appl. No.: 13/712,073

(22) Filed: Dec. 12, 2012

(65) Prior Publication Data

US 2013/0187641 A1 Jul. 25, 2013

Related U.S. Application Data

(63) Continuation-in-part of application No. 12/927,756, filed on Nov. 22, 2010, now Pat. No. 8,395,376.

(51) Int. Cl.
*G01R 33/12* (2006.01)

(52) U.S. Cl.
USPC .......................................................... 324/229

(58) Field of Classification Search
USPC ............ 324/228, 229, 233, 236, 240, 207.13, 324/207.16, 207.17, 209, 239
See application file for complete search history.

*Primary Examiner* — Melissa Koval
*Assistant Examiner* — Trung Nguyen
(74) *Attorney, Agent, or Firm* — Howard Cohen

(57) ABSTRACT

A method for identifying, measuring, and monitoring metal loss through corrosion ferromagnetic piping includes drive coils secured to the pipe and driven to emit a magnetic field which is transmitted through the object by magnetic domains in the object. Response coils detect the magnetic domains and generate a response signal. Response coils may be saddle or loop coils, or printed coils on flexible substrates that are applied to conform to the pipe peripheral surface. The system operates reiteratively over an extended period of time to detect loss of magnetic domains which is an important indicator of corrosion and deterioration of the object.

22 Claims, 5 Drawing Sheets

METHOD AND APPARATUS FOR MAGNETIC RESPONSE IMAGING

CROSS-REFERENCE TO RELATED APPLICATIONS

This application is a continuation-in-part of application Ser. No. 12/927,756, filed Nov. 22, 2010, for which priority is claimed.

FEDERALLY SPONSORED RESEARCH

Not applicable.

SEQUENCE LISTING, ETC ON CD

Not applicable.

BACKGROUND OF THE INVENTION

1. Field of the Invention

The present invention relates to apparatus and methods which can be utilized for identifying, measuring, and monitoring metal loss through corrosion or other deleterious factors in ferromagnetic piping and ferromagnetic vessels.

2. Description of Related Art

The following patents and publications exemplify the state of the art in systems for detecting corrosion in metallic systems, particularly pipes and pipelines.

Patent Publication No. US2002/0153249 by Eric Atherton describes a metallic corrosion monitoring system which employs the measurement of electrical current flow in the metal. This method is not as sensitive as the present invention and its measurement of magnetic flux for the detection of corrosion. There are a number of similar patents which depend upon the electrical conductivity of the metal to detect corrosion. In practice, it is difficult to detect the small changes in conductivity of a metal as it corrodes, since the effects of the corrosion will generally be very small compared to the remaining metal. The present invention does not utilize the conductivity of the metal in its application.

U.S. Pat. No. 4,400,782 by Masashi Ishikawa describes a system of using a pipe as a transmission line using the conductivity of the pipe. It is not practicable for continuous monitoring of a pipeline for corrosion because the system stability of the transmission line is not sensitive to small levels of corrosion. The present invention does not utilize the conductivity of the pipe in monitoring the pipe.

U.S. Pat. No. 4,107,605 by Robert Hudgell describes a method of testing metallic pipelines using eddy current sensing coils It is not suitable for long term monitoring of pipelines for corrosion as per the present patent application, and the present invention does not use eddy currents.

Patent Publication No. US2009/0058406A1 by Mochimitsu Komori describes a method of measuring the corrosion state of a magnetic material. It utilizes a two stage method of magnetization and is distinct from the present invention which uses a continuous AC magnetization procedure.

U.S. Pat. No. 0126422 by Alfred Crouch, et. al., describes a method of measuring a surface defect in an electrically conducting material using a pair of resonant coils. It is basically an eddy current array which is substantially different from the present invention which does not use eddy current technology.

U.S. Pat. No. 7,521,917 by Katragadda et. al., describes a method of detecting material integrity which drives a current through the material and then utilizes a sensing system for the magnetic field induced in the material. It is designed for testing train rails. The present invention is specifically designed for pipelines, and is substantially different in configuration and in application.

U.S. Pat. No. 7,362,097 by Brown, et. al., describes a pipeline inspection system where the apparatus design is for the movement of flexible coils that are pushed through the interior of the pipeline. The present invention uses fixed coils on the exterior of the pipeline and does not use any movement of these coils.

Patent Publication No. US2010/0017137A1 by Legandre Emmanual describes a method of measuring the physical parameters of a pipe by comparing the magnetic permeability to the electrical conductivity using coils within a pipe. The method is substantially different from the present invention in method and in coil configurations.

U.S. Pat. No. 7,6229,116 by Gerald Meeten, et. al., describes a three coil system for measuring structural features of a bore hole casing. The system moves through the interior of the bore hole and is very different from the present invention.

U.S. Pat. No. 4,611,170 by Roderick Stanley, et. al. describes a method of inspecting ferromagnetic pipes which features three movable axially split spools of wire and saturation levels of magnetic flux in the pipe. It is moved along the pipe and utilizes differential voltages of the two end pickup coils. The system is not a monitoring system for the pipe as per the present patent description.

There are many patents for measuring metallic integrity using eddy current systems. The present invention is not an eddy current system, and does not use eddy current technology. Also, the present invention utilizes computer(s), and digital processor(s) in order to provide a stable method of monitoring and correcting for the variable factors which affect the detection of corrosion and deterioration of pipelines and vessels.

BRIEF SUMMARY OF THE INVENTION

The present invention describes apparatus and methods which can effectively and economically be employed to detect, measure, and monitor the status of iron and steel pipes and pipelines as to deterioration or corrosion. The system can monitor insulated as well as un-insulated pipelines. It can be utilized below ground and in sea water. It can be employed when the pipe is covered by sheet aluminum and other non-ferromagnetic shielding. And it can maintain long term monitoring. It has been tested in many pipes, and it has functioned very well. It is sensitive to corrosion loss and can readily detect and measure metal corrosion losses of one tenth of one percent of metal loss.

DETAILED DESCRIPTION OF THE INVENTION

Figure 1A:
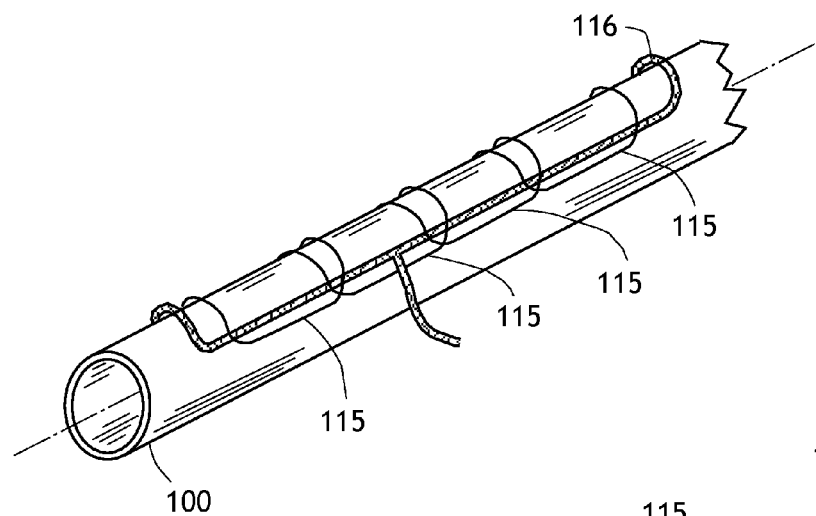
FIG. 1A is a perspective view of one embodiment of the drive coils and response coils of the magnetic response imaging system of the present invention.
Figure 1B:
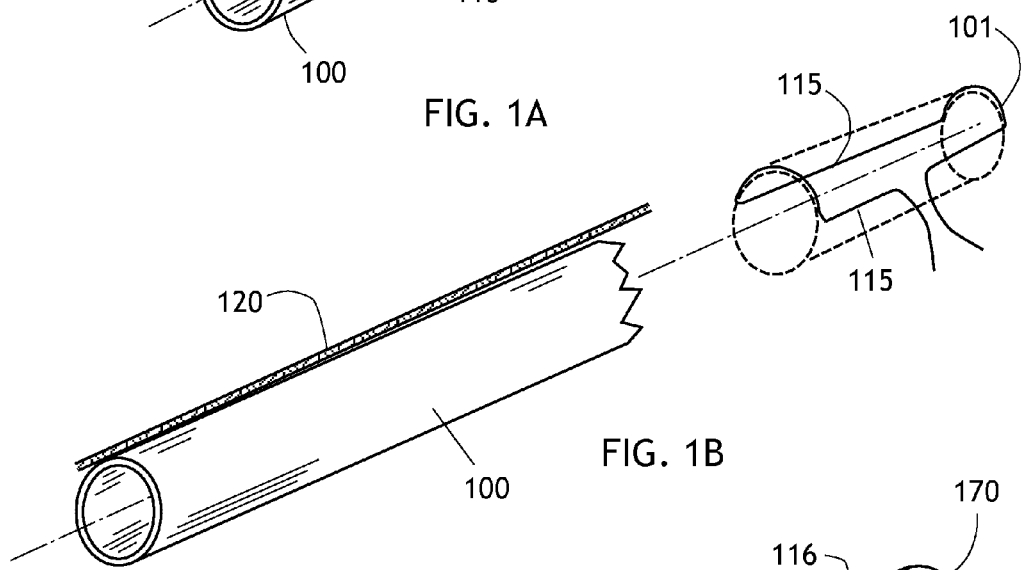
FIGS. 1B and 1C are perspective views of further embodiments of the drive coils of the invention.

FIG. 1A schematically shows part of one of the configurations of our advanced Magnetic Response Imaging (MRI), system. A pipeline section 100 has receiving coils 115 which are saddle coils in this configuration. The saddle coils 115 are generally multiple turn coils, though they are illustrated as single turn coils for ease of illustration. These coils are placed on the pipeline with the longitudinal axis parallel to the axis of pipeline 100. Several receiving coils are shown along the pipeline. They are showing overlapping, or they can also be placed consecutively end-to-end along the pipeline. Each receiving coil can be interrogated periodically by remote switching to each coil consecutively or in some designated order. Each receiving coil provides a voltage value which is determined by the status of the metal under each coil in the pipeline. FIG. 1B shows one form of the receiving coils more clearly. Again, only one turn is shown to provide clarity though multiple turns are generally employed.

The drive coil 116 has the form of a saddle coil similar to the coil 115 shown in FIG. 1B, and is generally lengthier than coil 115 in FIG. 1A. The drive coil 116 can overlap several receiving coils 101 as shown so as to provide a varying magnetic field over these receiving coils. The variable magnetic field causes the magnetic domains to alternate which induces voltages in the receiving coils. The voltage induced in each receiving coil is proportional to the amount of steel in the portion of the pipeline which is directly under that specific receiving coil. Using a specific current in the drive coil will provide a specific induced voltage in each receiving coil. That specific induced voltage is proportional to the number of magnetic domains in the section of pipeline which is directly under each receiving coil. Therefore, one is able to monitor the health of the pipeline by measuring the induced voltage in each of the receiving coils 101 in turn and taking successive measurements to determine changes in the induced voltage due to the amount of steel which has corroded or deteriorated, as well as the amount of steel remaining in each pipeline sector.

FIG. 1B shows a single drive wire 120 along a pipeline. This single wire is also capable of supplying the magnetic drive for the system. It is more common to use multiple turn saddle coils 116 for the magnetic drive as shown in FIG. 1A. In FIG. 1A only one sector of the pipeline is illustrated, however, this configuration is generally repeated along the pipeline so that a significant portion of the pipeline can be monitored.

Figure 1C:
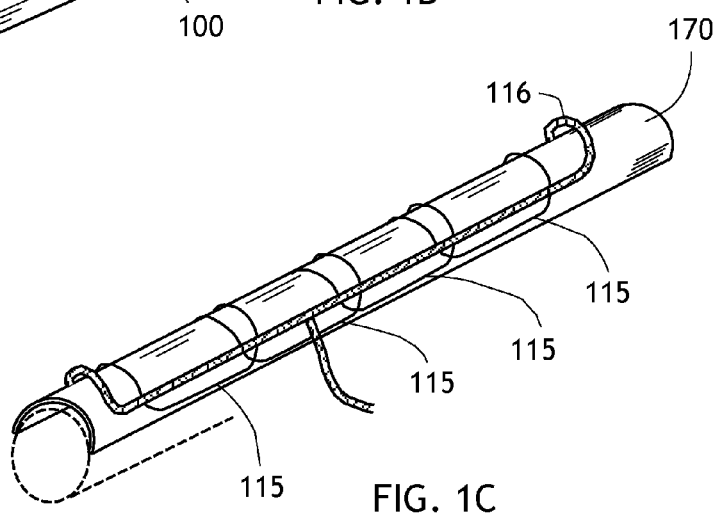

FIG. 1C shows a variation of the arrangement shown in FIG. 1A wherein the same coil figurations 115 and 116 are mounted on a plastic or other non-ferromagnetic semi-circular tube 170. The coil mount need not be semi-circular, it can be rectangular and adjustable in size so as to be able to be placed over pipelines of various sizes. This more portable arrangement of the drive and receiver coils may be used to be installed or placed into position more readily by simply placing the entire tube 170 on the pipeline. The other important aspect of using a portable configuration 170 is that the entire semi-circular tube with coils can be moved along a pipeline and it will then detect and register non-uniformities in that pipeline. These non-uniformities may be corrosion, welds, or other defects in the pipeline. It is a very useful means of detecting pipeline problems inexpensively, or when a permanent coil installation is not desired.

Figure 2A:
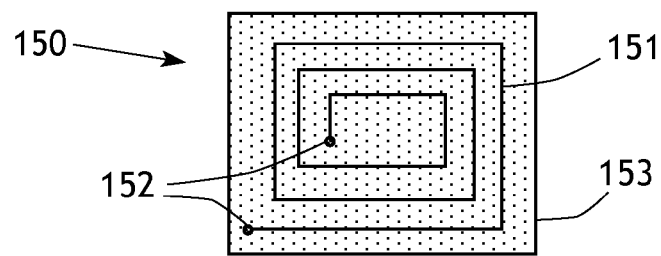
FIG. 2A is a plan view of a further embodiment of the response coils of the invention.
Figure 2B:
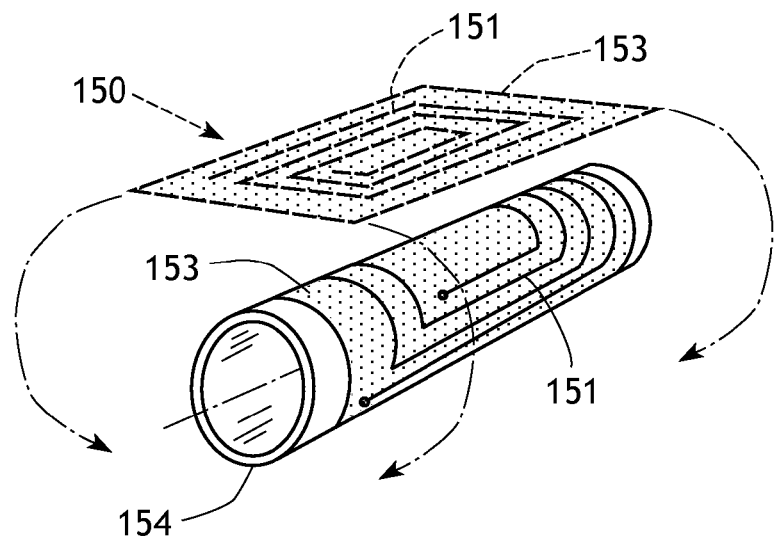
FIG. 2B is a perspective view of the response coil of FIG. 2A applied to a cylindrical object.
Figure 2C:
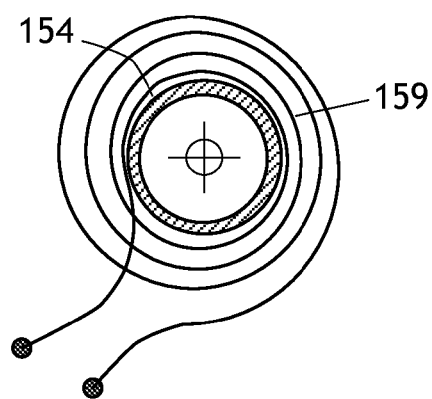
FIG. 2C is a plan view of a response coil embodiment that circumscribes the cylindrical object.

FIG. 2A illustrates another embodiment 150 of the receiving coils of the invention. Receiving coil 150 is comprised of one or more conductors 151 adhered to a flexible substrate 153. These coils 150 may be economically constructed using printed circuit technology or alternatively by any other known coil winding procedure. FIG. 2B shows the coil 150 installed on a section of a pipeline 154 by wrapping the flexible substrate about the pipe and securing it thereto by adhesive, tape, binding, or the like. The terminals 152 of the coil are brought out to be connected to a voltage readout system which is described below. As shown in FIG. 2C, another embodiment 159 of the receiving coils may be a simple round coil comprised of a plurality of turns of wire about a common axis of symmetry and circumscribing the pipe 154.

Figure 3:
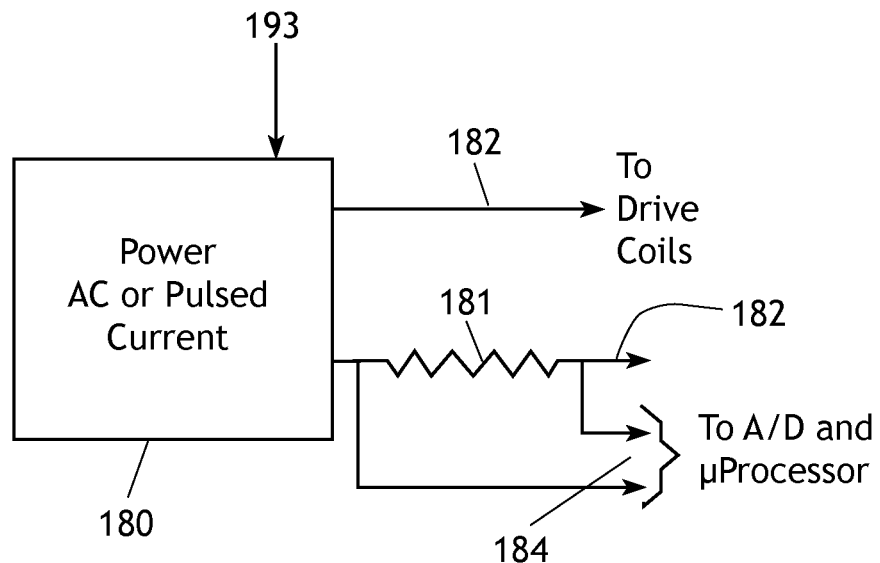
FIGS. 3-5 are block diagrams illustrating the major components of the invention.

FIG. 3 illustrates the drive current source 180. The input 193 can be a solar source, a standard AC power line, or any other source of AC or DC power. The unit 180 provides a current source 182 that is alternating or pulsed and is connected to the drive coil 116 or 120. In actual use the power source will likely be switched into many different drive coils along the pipeline. The power requirement for a long pipeline can be very moderate because of the same power source being shared through switching into many drive coils. Resistor 181 which senses the current provides signal 184, a small amount of the total current 182 which is provided to the drive coils is utilized to determine the actual drive current and thereby be utilized to correct the data from the receiving coils for variations in the drive current. By using a sensor 181 of the current drive, the adjusted value of the drive current 182 can be provided to a microprocessor or computer and the computer can readily apply a correction factor to the receiver voltages by taking account of the variations in current drive. In addition, other sensors such as temperature sensing of the pipeline are readily sensed and their values can easily be monitored by a microprocessor or computer to correct for these variations in the magnetic driver. The program for such corrections is very straightforward; it is termed a learning program in computer science, and is very standard.

With an extensive set of drive and receiving coils along the pipeline, each set of which is a repetition of the short section illustrated in FIG. 1A, multiple drive coils such as 116 in FIG. 1A may be switched into the power source 180 shown in FIG. 3. Each in turn provides magnetic domain variations so that the receiving coils under each drive coil will be energized. The voltage of each receiving coil in turn provides a measure of the integrity of the pipeline under that receiving coil which is switched in and sampled in turn. Even less than one part in a thousand of metal loss in the pipeline under each receiving coil provides a significant signal difference and the pipeline deterioration over time can be accurately monitored.

Figure 4:
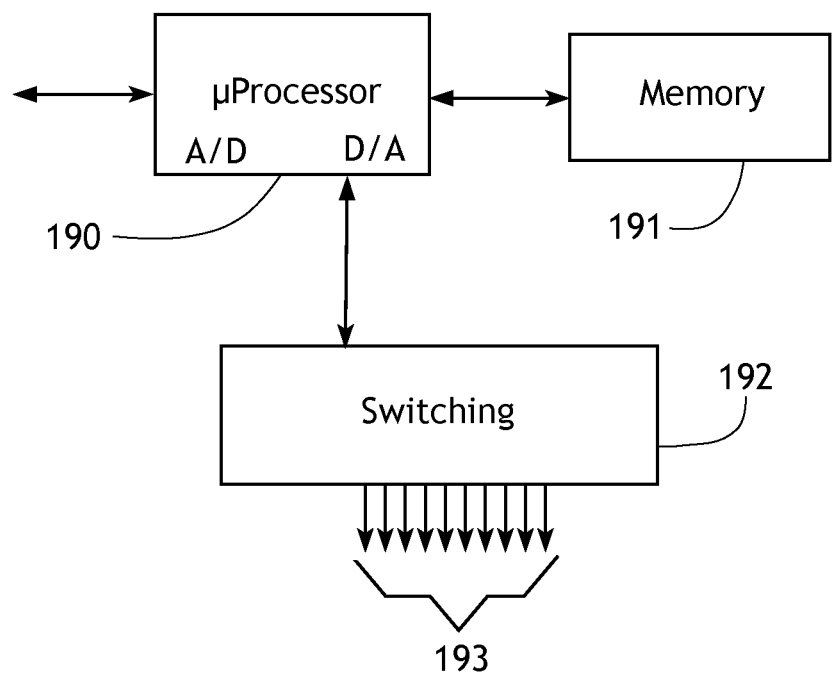
Figure 5:
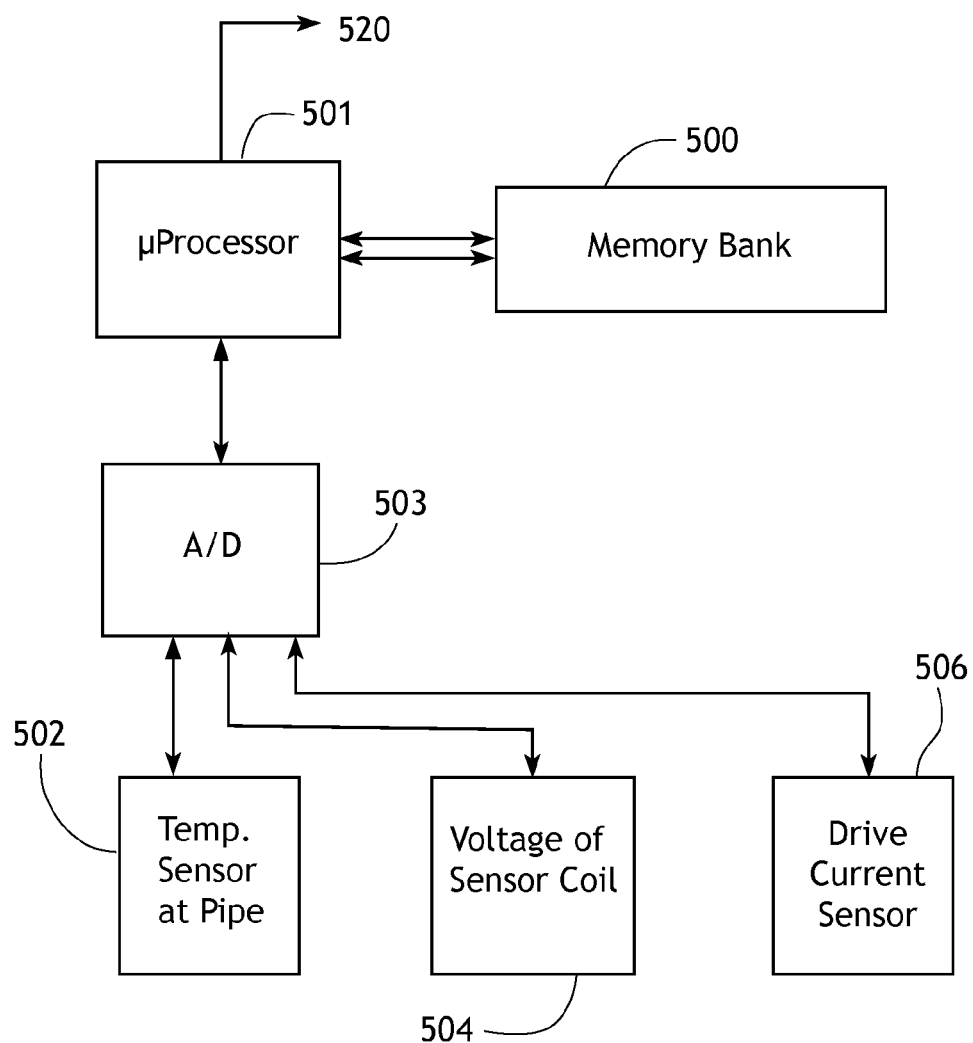
Figure 6:
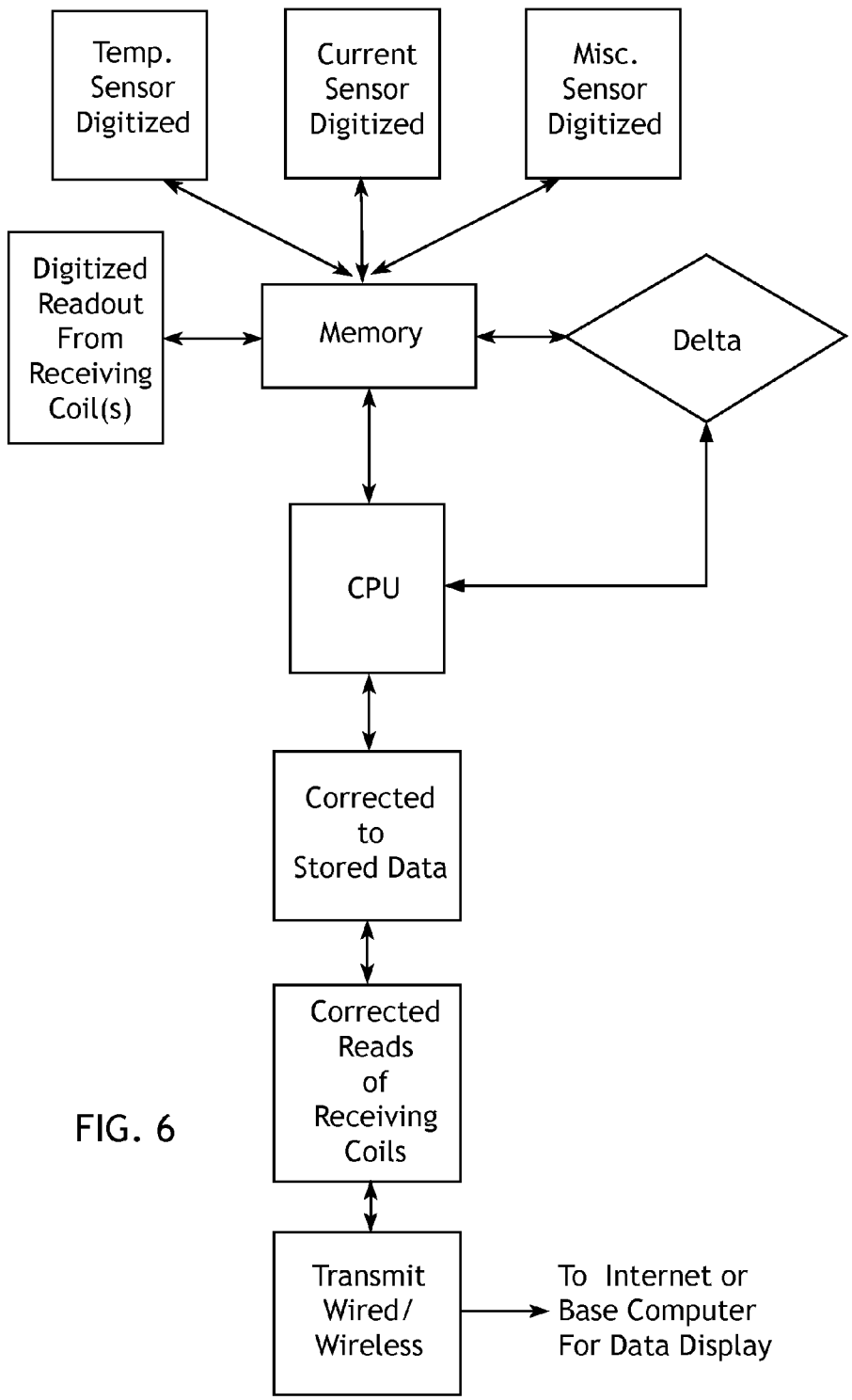
FIG. 6 is a flow chart depicting the process steps according to the invention to determine metal loss in a ferromagnetic object.

There are many choices as to how to connect the receiving coils to the microprocessor or computer system 190 in FIG. 4 or FIG. 5. Generally, the output leads 193 of the switching system 192 can connect each receiving coil in turn and sample the individual receiving voltages from each coil 115. However, the receiving coils 115 may also be connected in series in a manner in which each coil opposes the voltage picked up by one specifically designated 115 coil. That specifically designated coil is used as a reference coil, and the temperature sensing correction system of FIG. 6 as well as the current correction system of FIG. 6 is utilized by the microprocessor to provide corrected data from that specific designated reference coil. Once the designated reference coil data is corrected for variations in current drive and temperature, then that coil is utilized to compare its output voltage with the each of the other receiving coils 115. The advantages of having a single designated reference coil corrected for temperature and current are that the voltage output of that designated coil may be compared with all of the other receiving coils 115 in each array. By utilizing such voltage comparisons, the dynamic voltage range of the receiving coils is compressed, and the analog to digital conversion 190 is improved in accuracy.

Each drive coil along a lengthy pipeline can be switched into the current source 180 one at a time in sequence to provide power to each drive coil in turn in order to economize on power and the use of the current source. The drive coils can take the form of a single current carrying wire or multiple current carrying wires. The drive coils 116 or 120 are activated by connection to 182 to a varying regulated current source 180. The source can be AC, pulsed, or otherwise varied. The frequency of the varying drive current can be swept through very low and higher frequency. By sweeping or by selecting lower and higher frequencies for the drive, the penetration of the magnetization in the pipeline is respectively greater and lesser. The receiver coils therefore receive selective signals which emphasize the corrosion, cracking, or deterioration of the pipe on the inner part of the pipe in the case of lower frequency drive currents, and will emphasize the corrosion, cracking, or deterioration of the outer part of the pipe in the case of the higher frequency drive currents. The current can be measured through a small series resistance 181, or alternatively by any other current sensor, and the voltage across the series resistance, or other form of current sensor is a measure of the current drive. By measuring that voltage, and combining that data into a digital processor with data from temperature, excellent long term reliable readouts of the total measurement of the pipeline corrosion or other pipeline deterioration is accomplished. By noting the history of the temperature and the average current for a period of time, the stability of the system can be established by storing the changes in the signals from pickup coils 115, 150, or 159 relative to the changes in the drive current and relative to the temperature. By storing these in a digital memory, the readouts can be adjusted for current variations and temperature such that the readings are very reliable and can be compared over long time periods.

The signal pickup coils, or receiver coils 115 are multiple turn coils which can be saddle coils surrounding the pipeline. They can be wound wire coils or they can be printed circuit coils on a flexible substrate 150 so as to wrap around the pipeline. These coils can be put in series so as to have two or more surround the pipeline if needed for large pipeline diameters. They can also be circular coils 159 encompassing the pipeline 100 when it is convenient to utilize circular coils such as with new pipelines or using a special winder to install circular coils on an existing pipelines. Usually, for existing pipelines, it is simpler to utilize multiple saddle coils 115 because of the ease of installation. The view shown in FIG. 2B of the saddle coils 150 is a view of the coils on the flexible substrate 153 prior to wrapping the substrate around the pipeline. The flexible substrate 153 is shown in the form of a cylinder which is how it appears when wrapped around the pipeline. Typically, one uses printed circuits on a flexible substrate for these coils, but wire wound coils will function just as well. Among the advantages of using printed circuit coils is that the uniformity is well determined.

The use of drive coils which are parallel to the pipeline is advantageous relative to other placements because the phase of the AC or pulsed current source is constant all along the drive coil length. Therefore the receiver coils will all receive the same response when the pipeline is uniform, and variations in the response can be attributed only to non-uniformities and, most importantly, metal loss from corrosion or deterioration. Therefore this system is particularly effective for pipeline monitoring. For a pipeline many drive coils are required. These coils are interrogated by a switching system to each coil or coils in series and coils in parallel and coils in opposition as sensitivity to the corrosion level detection can be set. Each drive coil region is denoted as a specific locale which is numbered, 1, 2, 3, etc. The drive coils and the receiver coils in locale 1 are activated by automatic switching, then locale 2 drive and receiver coils are activated, then locale 3 is activated, etc. In this manner, the total power requirement is small because each locale is activated and that respective set of receiving coils is sensed in turn. The switching process and timing is determined by a computer system or equivalently by a microprocessor with an analog to digital converter and a digital to analog converter 190 and a digital memory 191.

This system may be modified slightly to provide the determination of pipe integrity. Frequently, used pipes are employed in oil drilling, in gas and oil lines, and in water lines. It is important to know the condition of these pipes, and whether they are in good enough condition to be safely utilized. The system for testing these pipes is similar, with a change in the geometric design.

FIG. 1C illustrates a one turn coil 120 or several turn coil which extends along the whole ferromagnetic pipe length. The coil is driven by an alternating or periodic source 180, typically AC and a circular coil 159 (FIG. 2C), or a saddle coil 115 (FIG. 1B) is moved slowly along the pipe length. Any loss in the amount of steel under the sensing circular coil 159 or a sensing saddle coil 115 will be seen by a drop in the voltage reading indicating the degree of corrosion in the pipe at each position of the sensing coil. The calibration of the system is straightforward by using a standard which typically can be a new pipe or a pipe which has a known wall thickness such as one measured by an independent system such as an ultrasonic system, or an un-corroded pipe with wall thickness like the pipe which is to be monitored.

There is a significant advantage in utilizing a drive coil which extends along the pipeline because that provides a drive signal which has zero phase shift all along its length. By having zero phase shift, and having the drive along the pipeline, the receiver coils are all in phase, and are closely coupled to the magnetic domains. That provides increased sensitivity and a very economical use of copper. Also, the use of printed circuits on a flexible substrate is a great advantage since it provides very consistent coils which are easily installed by wrapping them about the pipeline.

One must stabilize the monitoring system or else compensate for temperature and variations in the drive current. The temperature can be monitored using a thermocouple or other temperature measuring apparatus and compensate based upon the tabulation of a table of variations of the response coils due to measured temperatures. Such a table can be generated by recording the effective voltage variations in the receiving coils due to the temperature variations. The optimum way of generating such a table is by the use of a computer system and storing the table in a non-volatile memory; for example, a microprocessor 501 and a memory bank 500 as illustrated in FIG. 5. After a table of temperature versus receiver signal is recorded, in an actual installation, the microprocessor 501 will interrogate the memory bank 500 for corrections to the sensor coil reading 504 and rely upon the table in the memory bank 500 for reading corrections. The analog to digital converter 503 is used to convert the input voltages from the temperature sensor 502, and the voltage of the sensor coil 504 to digital forms where the microprocessor can determine the variations in the temperature as they effect the sensor voltage output 504.

The second variable is the current in the drive coils. These are detected by drive current sensor and 506 converted into digital form by A/D 503 and the microprocessor 501 compares the drive current variations with the receiving voltage 504 from the receiver coils on the pipeline. Once again, a table of corrections is generated by the microprocessor 501 and the table is stored in the memory bank. In most cases, it is sufficient to run the whole system for a day or a week to establish the signal correction tables for the temperature and the current drive variations. An extrapolation to higher or lower temperatures and higher and lower current values from the stored values can be programmed into the microprocessor or computer.

After the microprocessor makes the corrections for temperature and drive current variations, it outputs the corrected signal 520. The corrected signal is stored in memory and can be sent to a base station by wire or wireless. In remote locales, it can be sent using data transfer via a cell phone system which communicates via satellite. For other locales, conventional data transmission can be accomplished by conventional telemetering using modems and a convenient frequency for the data transmission.

FIG. 6 illustrates one form of the logic which provides output data on the status of the pipeline derived from the voltages. Here the digitized data from the current sensor, the temperature sensor, and any additional sensor such as pressure or vibration, etc. is inputted into a temporary memory. Signal averaging is generally employed whenever noise is significant. The signal values are compared with stored data from previously "learned" use of the system with variations of these parameters in the step denoted Delta. Such computer learning procedures are well known to all computer scientists. The actual readouts of the digitized signals of the receiving coils each in turn are then corrected for the values taken with the timely sensors of temperature, current, etc. and processed by the CPU, (central processor unit of the microprocessor or the base computer), and are transmitted to a central data station or put on the internet.

The foregoing description of the preferred embodiments of the invention has been presented for purposes of illustration and description. It is not intended to be exhaustive or to limit the invention to the precise form disclosed, and many modifications and variations are possible in light of the above teaching without deviating from the spirit and the scope of the invention. The embodiment described is selected to best explain the principles of the invention and its practical application to thereby enable others skilled in the art to best utilize the invention in various embodiments and with various modifications as suited to the particular purpose contemplated. It is intended that the scope of the invention be defined by the claims appended hereto.

The invention claimed is:

1. A method for monitoring corrosion and deterioration of a pipe having a pipe wall, including the steps of:
   providing at least one drive coil and securing said at least one drive coil to the exterior surface of said pipe wall;
   providing at least one response coil and securing said at least one response coil to the exterior surface of said pipe wall;
   transmitting a drive current through said at least one drive coil to create a magnetic signal that propagates through the magnetic domains of said pipe wall;
   said at least one response coil receiving said magnetic signal and turn generating a response signal in said response coil;
   quantifying said drive current and said response signal and recording said drive current and response signal; and,
   comparing said drive current and response signal to respective reference levels to determine corrosion and deterioration in said pipe wall.

2. The method of claim 1, wherein said step of providing at least one drive coil includes extending at least one winding a substantial distance longitudinally along said pipe.

3. The method of claim 1, wherein said transmitting step includes transmitting an alternating or pulsed drive current.

4. The method of claim 1, said step of providing at least one response coil including providing a printed circuit coil device.

5. The method of claim 4, further including the step of forming said printed circuit coil device on a flexible substrate.

6. The method of claim 5, further including the step of bending said flexible substrate about said exterior surface of said pipe wall to conform to said exterior surface.

7. The method of claim 2, further including the step of providing a plurality of said response coils arrayed on said exterior surface of said pipe wall, each of said response coils having a longitudinal extent that is far less than said at least one winding of said drive coil.

8. The method of claim 7, wherein said transmitting step includes transmitting an alternating or pulsed drive current, and said response signals of said plurality of response coils have a generally fixed phase relationship.

9. The method of claim 1, further including the steps of:
   measuring variations in said drive current and ambient conditions of said pipe; and,
   correcting said response signal to compensate for said variations in said drive current and ambient conditions.

10. The method of claim 9, wherein said step of measuring variations includes measuring variations in the temperature of said pipe.

11. The method of claim 1, further including the step of providing a plurality of said response coils arrayed on said exterior surface of said pipe wall, each generating a respective response signal.

12. The method of claim 11, further including the step of measuring variations in said drive current and ambient conditions of said pipe; and,
   correcting the response signal of one of said response coils to compensate for said variations in said drive current and ambient conditions, the corrected response signal thereafter comprising the response signal reference level.

13. The method of claim 1, wherein said step of providing at least one response coil includes providing a plurality of loop coils having at least one winding circumscribing said pipe.

14. The method of claim 1, wherein said step of providing at least one response coil includes providing a plurality of saddle coils arrayed on said exterior surface of said pipe wall.

15. The method of claim 1, further including reiterating said transmitting, receiving, and quantifying steps over an extended time period, and recording said drive current and response signal.

16. The method of claim 15, wherein said comparing step comprises measuring changes in said recorded response signal over time with respect to said respective reference level to determine corrosion and deterioration in said pipe wall.

17. The method of claim 15, further including the step of averaging said response signal over a plurality of said reiterated steps.

18. The method of claim 1, further including the step of mounting said at least one response coil on a non-planar substrate, and impinging said non-planar substrate on said exterior surface of said pipe wall to generate said response signal.

19. The method of claim 18, further including the step of mounting said at least one drive coil on said non-planar substrate.

20. The method of claim 19, wherein said impinging step includes slidably and removably impinging said non-planar substrate on said exterior surface of said pipe wall.

21. The method of claim 18, wherein said non-planar substrate is provided with a curvature that conforms to a curved portion of said exterior surface of said pipe wall.

22. The method of claim 1, wherein said transmitting step includes transmitting a drive signal that is varied from very low to higher frequencies to discriminate different regions of deterioration in the pipeline.

* * * * *